United States Patent [19]

Soula et al.

[11] 4,081,388
[45] Mar. 28, 1978

[54] COMPOSITIONS BASED ON ALKENYLSUCCINIMIDES AS ADDITIVES FOR LUBRICATING OILS

[75] Inventors: Gerard Soula, Meyzieu; Philippe Duteurtre, Le Havre, both of France

[73] Assignee: Orogil, Paris, France

[21] Appl. No.: 673,975

[22] Filed: Apr. 5, 1976

[30] Foreign Application Priority Data

Apr. 18, 1975 France ............................ 75 12136
Dec. 24, 1975 France ............................ 75 39691

[51] Int. Cl.² ............................................. C10M 1/32
[52] U.S. Cl. ..................... 252/51.5 A; 260/326.5 F
[58] Field of Search ............................ 252/51.5 A; 260/326.5 F

[56] References Cited

U.S. PATENT DOCUMENTS

| | | | |
|---|---|---|---|
| 2,662,898 | 12/1953 | Ross et al. .................... | 260/326.5 F |
| 3,272,746 | 9/1966 | LeSueur et al. ............. | 252/51.5 A X |
| 3,324,033 | 6/1967 | Knapp ........................... | 252/51.5 A |
| 3,458,444 | 7/1969 | Shepherd et al. ............. | 252/51.5 A |
| 3,620,977 | 11/1971 | Honnen et al. ................ | 252/51.5 A |
| 3,806,456 | 4/1974 | Vogel ............................. | 252/51.5 A |
| 3,879,306 | 4/1975 | Kablaoui et al. ............. | 252/51.5 A |

FOREIGN PATENT DOCUMENTS

1,444,904   9/1963   Germany .................... 252/51.5 A

*Primary Examiner*—Delbert E. Gantz
*Assistant Examiner*—Andrew H. Metz

[57] ABSTRACT

New compositions, based on alkenylsuccinimides, are provided which impart useful dispersing, detergent, anti-rust and anti-foam properties when employed as an additive in a lubricating oil. The new compositions are alkenylsuccinimides obtained by condensing an alkenylsuccinic anhydride with at least one polyamine of the formula:

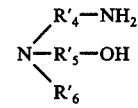

in which formula $R'_4$ is a -r-O-r' radical, $R'_5$ is one of the radicals -r-O-r'-$NH_2$, -r'-$NH_2$, or -r-OH, $R'_6$ is one of the radicals -r-O-r-$NH_2$, -r'-$NH_2$, -r-OH, $C_1$-$C_4$-alkyl or phenyl, and r and r' have the definition given fully below using a molar ratio of polyamine to alkenylsuccinic anhydride of less than 1.

26 Claims, No Drawings

COMPOSITIONS BASED ON ALKENYLSUCCINIMIDES AS ADDITIVES FOR LUBRICATING OILS

BACKGROUND OF THE INVENTION

The present invention relates to new compositions based on alkenylsuccinimides, the process for their preparation, as well as their application as additives for lubricating oils.

It is already known to react alkenylsuccinic anhydrides with aliphatic monoamines, aromatic and heterocyclic amines and the like, alkylidenepolyamines, polyoxyalkylideneamines and the like, and to use the alkenylsuccinimides thus obtained as additives for lubricants.

It has now been found, in accordance with the present invention, that compositions based on new alkenylsuccinimides are particularly suitable for use as detergent/dispersing agent additives, anti-rust additives and anti-foam additives for engine oils.

It is, accordingly, an object of the present invention to provide new compositions which are highly suitable as lubricating oil additives.

It is also an object of the present invention to provide advantageous processes for producing the new additives.

It is further object to provide novel lubricating oil compositions containing the new additives.

Further objects of the present invention will be apparent to those skilled in the art from the present description.

GENERAL DESCRIPTION OF THE INVENTION

The compositions which form the subject of the invention contain at least one succinimide of the formula:

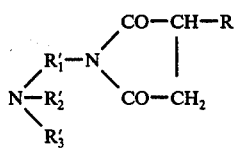

(I)

in which formula R is an alkenyl group containing from 20 to 200 carbon atoms, $R'_1$ is a —r—O—r' radical, $R'_2$ is one of the radicals

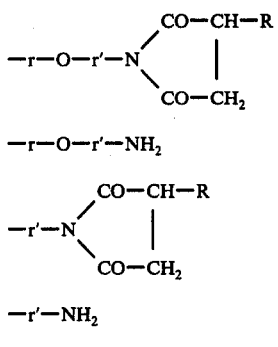

and $R'_3$ is one of the radicals

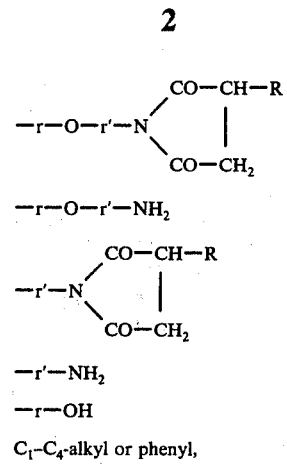

$C_1$-$C_4$-alkyl or phenyl, the radical r representing an optionally branched $C_2$-$C_3$-alkyl group, preferably an ethyl or isopropyl group and the radical r' representing a propyl or isobutyl group.

The new compositions which form the subject of the invention can be prepared by a condensation reaction, involving the action of an alkenylsuccinic anhydride, in which the alkenyl group contains from 20 to 200 carbon atoms, with at least one polyamine of the formula

(II)

in which formula $R'_4$ is a —r—O—r' radical, $R'_5$ is one of the radicals —r—O—r'—$NH_2$, —r'—$NH_2$ or —r—OH, $R'_6$ is one of the radicals —r—O—r'—$NH_2$, —r'—$NH_2$, —r—OH, $C_1$-$C_4$-alkyl, or phenyl, and the radicals r and r' have the definition given above.

This condensation reaction takes place at a temperature of between 120° and 230° C., preferably between 140° and 180° C., with a molar ratio of polyamine to alkenylsuccinic anhydride of less than 1. The reaction is optionally carried out in the presence of a diluent to reduce the viscosity of the reaction mixture; the said diluent will preferably be chosen from among the lubricating oils which can be used as base oils in the lubricating compositions; examples of these base oils will be given later.

If the amine employed is a monoamine, the molar ratio of amine to alkenylsuccinic anhydride is between 0.8 and 0.95, preferably between 0.85 and 0.90.

If the amine employed is a diamine, a molar ratio of between 0.4 and 0.6 makes it possible to obtain compositions containing a major proportion of bis-alkenylsuccinimide, while a molar ratio of about 1, and preferably of between 0.7 and 0.95, makes it possible to obtain compositions containing a major proportion of monoalkenylsuccinimide.

If the amine employed is a triamine, a ratio of between 0.3 and 0.35 makes it possible to obtain compositions containing a major proportion of tris-alkenylsuccinimide, a molar ratio of between 0.4 and 0.6 makes it possible to obtain a major proportion of bis-alkenylsuccinimide, and a molar ratio of about 1, preferably between 0.7 and 0.9, makes it possible to obtain a major proportion of monosuccinimide.

The alkenylsuccinic anhydrides employed are prepared in a known manner, for example, by thermal condensation (U.S. Pat. No. 3,306,907) of maleic anhydride with a polyolefin of mean molecular weight between about 400 and 4,000. The said polyolefin is chosen from among oligomers or polymers of optionally branched $C_2$-$C_{30}$ olefins, or copolymers of the said olefins with one another or with diene or vinyl-aromatic comonomers; among these polyolefins, the following may be mentioned as being preferred: the oligomers of $C_2$-$C_{20}$-α-mono-olefins, such as the oligomers of ethylene, propylene, 1-butene, isobutene, 3-cyclohexyl-1-butene and 2-methyl-5-propyl-1-hexene, the copolymers of these α-olefins with one another or with internal olefins, as well as the copolymers of isobutene with a comonomer chosen from among butadiene, styrene, 1,3-hexadiene or conjugated or non-conjugated dienes and trienes.

The condensation reaction can also be carried out in the presence of chorine (U.S. Pat. No. 3,231,587 and Belgian Patent No. 805,486), iodine (British Patent No. 1,356,802), or bromine (Soula, United States patent application, Ser. No. 574,720, filed May 5, 1975—corresponding to French application No. 74/18915, filed May 31, 1974—assigned to related company, Rhone-Poulenc Industries); this operation can also be carried out starting from monochlorinated or monobrominated polyolefins, as indicated in the French patent published under No. 2,042,558.

The polyamines preferentially employed for preparing the new compositions are, for example: tris-(3-oxo-6-amino-hexyl)-amine, N-ethyl-N,N-bis(3-oxa-6-amino-hexyl)-amine, N-(3-aminopropyl)-N,N-bis-(2-methyl-3-oxa-6-amino-hexyl)-amine, tris-(2-methyl-3-oxa-6-amino-hexyl)-amine, tris-(2,5-dimethyl-3-oxa-6-amino-hexyl)-amine, tris-(3-oxa-5-methyl-6-amino-hexyl)-amine, N-(2-hydroxyethyl)-N,N-bis-(3-oxa-6-amino-hexyl)-amine, N,N-bis-(2-hydroxyethyl)-N-(3-oxa-6-amino-hexyl)-amine, N-ethyl-N-(2-hydroxyethyl)-N-(3-oxa-6-amino-hexyl)-amine, N-ethyl-N-(2-hydroxyethyl)-N-(3-oxa-5-methyl-6-amino-hexyl)-amine, tris-(3-oxa-5-methyl-6-amino-hexyl)-amine, N-(2-hydroxyethyl)-N,N-bis-(3-oxa-5-methyl-6-amino-hexyl)-amine, and N,N-bis-(2-hydroxyethyl)-N-(3-oxa-5-methyl-6-amino-hexyl)-amine.

In general terms, the polyamines to be employed are obtained by cyanoethylation of alkanolamines of the formula

(III)

in which formula r has the definition given above, X is hydrogen or a r—OH radical, and X' is hydrogen, a r—OH radical, a $C_1$-$C_4$-alkyl radical or phenyl, with acrylonitrile or methacrylonitrile, followed by a hydrogenation of the nitriles obtained.

The cyanoethylation reaction can be carried out in accordance with the process described in U.S. Pat. No. 2,326,721.

If a complete cyanoethylation of the alkanolamine employed, for the purpose of preparing polyamines with ether groups, of the formula II, in which neither $R'_5$ nor $R'_6$ represents a —r—OH radical, is desired, a ratio of the number of groups with mobile hydrogen to the number of nitrile groups which is less than or equal to 1 is necessary; in general, from 1 to 1.2 mols of acrylonitrile or of methacrylonitrile are used per group, with mobile hydrogen, of the alkanolamine.

If an incomplete cyanoethylation of the alkanolamine employed, for the purpose of preparing polyamines with ether groups, of the formula II, in which at least one of the groups $R'_5$ and $R'_6$ represents a r—OH radical, is desired, a ratio of the number of groups with mobile hydrogen to the number of nitrile groups which is greater than 1 is necessary; in general, if the alkanolamine of the formula III employed is a trialkanolamine or has the formula $NH$—$(CH_2$—$CHR_1$—$OH)_2$, the molar ratio of alkanolamine to acrylonitrile or methacrylonitrile can be between 0.34 and 2; if the alkanolamine employed is an alkyldialkanolamine or phenyldialkanolamine, the molar ratio of alkanolamine to acrylonitrile or methacrylonitrile can be between 0.55 and 2.

Among the alkanolamines of the formula III there may be mentioned triethanolamine, ethyldiethanolamine, triisopropanolamine and the like.

The hydrogenation reaction can be carried out by means of molecular hydrogen in the presence of Raney cobalt or Raney nickel, in accordance with the method described in "Methoden der Organischen Chemie" ("Methods of Organic Chemistry"), Houben-Weyl, 4th edition, Volume XI/1, page 559 (1957).

The present invention also relates to the lubricating oils improved by addition of about 1 to 10%, of their weight, of the compositions described above, which impart their detergent/dispersing properties, anti-rust properties and anti-foam properties to the said oils.

In accordance with the present invention, it has been found that the alkenyl-succinimides of the formula I, in which neither $R'_2$ nor $R'_3$ represents a r—OH radical, and very particularly the alkenyl-succinimides of the formula:

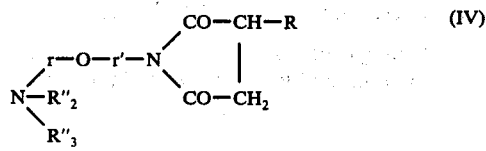

(IV)

in which formula r, r' and R have the definition given above, $R''_2$ represents the radical

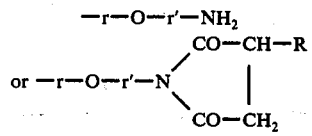

and $R''_3$ represents one of the radicals

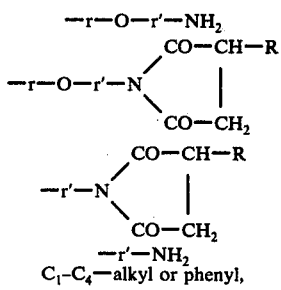

$C_1$-$C_4$—alkyl or phenyl, exhibit particularly remarkable detergent/dispersing properties as well as excellent anti-rust and anti-foam properties.

The applicants have also found that the alkenyl-succinimides of the formula:

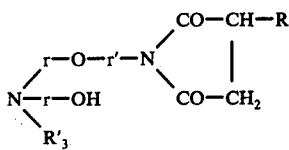

wherein R'₃ represents one of the radicals

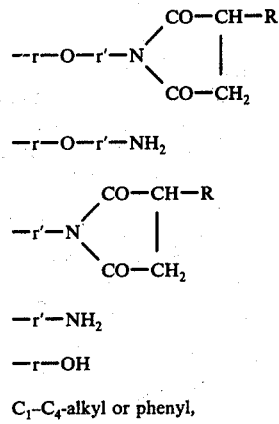

$C_1$-$C_4$-alkyl or phenyl, exhibit remarkable anti-rust properties as well as excellent detergent/dispersing properties and anti-foam properties.

Particularly remarkable dispersing properties and anti-rust properties are imparted to the oils by addition, to the said oils, of mixtures of alkenylsuccinimides of the formulas IV and V, above, for example, mixtures consisting of 99.5 to 50%, preferably 98 to 50%, of at least one alkenyl-succinimide of the formula IV and of 0.5 to 50%, preferably of 2 to 50%, of at least one alkenylsuccinimide of the formula V.

In particular, there may be mentioned the additives consisting of 98 to 50% of at least one polyisobutenylsuccinimide of the formula

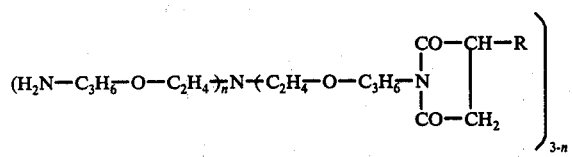

wherein n is equal to 0, 1 or 2, and of 2 to 50% of at least one polyisobutenylsuccinimide of the formula

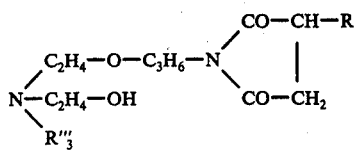

in which formula R'₃' represents one of the radicals

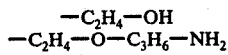

$$-C_2H_4-O-C_3H_6-N\begin{matrix}CO-CH-R\\|\\CO-CH_2\end{matrix}$$

wherein R represents a polyisobutenyl radical containing from 20 to 200 carbon atoms.

These additives can be prepared either by simple mixing of the various constituents or, preferably, by condensation, at a temperature of between 120° and 230° C., of a polyisobutenylsuccinic anhydride, in which the isobutenyl group contains from 20 to 200 carbon atoms, with a composition based on polyamines with ether groups, consisting of 98 to 50%, of its weight, of tris-(3-oxa-6-amino-hexyl)-amine and of 2 to 50%, of its weight, of N-(2-hydroxyethyl)-N,N-bis-(6-amino-3-oxa-hexyl)-amine and of of N,N-bis-(2-hydroxyethyl)-N-(6-amino-3-oxa-hexyl)-amine.

The said compositions employed, which are based on polyamines with ether groups, can be obtained either by simple mixing or directly by cyanoethylation of triethanolamine with acrylonitrile in a molar ratio of triethanolamine to acrylonitrile of between 0.34 and 0.5, followed by hydrogenation of the nitriles obtained.

Further additives which may be mentioned are those consisting of 98 to 50% of at least one polyisobutenylsuccinimide of the formula

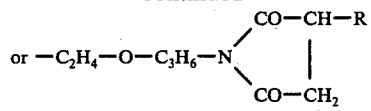

in which formula n is equal to 0 or 1, and of 2 to 50% of a polyisobutenylsuccinimide of the formula

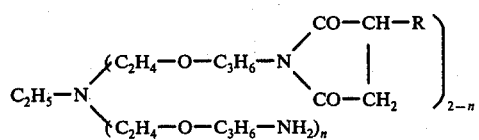

wherein R represents a polyisobutenyl radical containing from 20 to 200 carbon atoms.

The said additives can be prepared either by simple mixing of the various constituents or, preferably, by condensation, at a temperature between 120° and 230° C., of a polyisobutenylsuccinic anhydride, in which the polyisobutenyl group contains from 20 to 200 carbon atoms, with a composition based on polyamines with ether groups, consisting of 98 to 50%, of its weight, of N,N-bis(3-oxa-6-amino-hexyl)-ethylamine and of 2 to 50% of N-ethyl-N-(2-hydroxyethyl)-N-(6-amino-3-oxa-hexyl)-amine.

The said composition employed, based on polyamines with ether groups, can be obtained either by simple mixing or directly by cyanoethylation of ethyldiethanolamine with acrylonitrile in a molar ratio of ethyldiethanolamine to acrylonitrile of between 0.55 and 1, followed by hydrogenation of the nitriles obtained.

The lubricating oils which can be used can be chosen from among a great variety of lubricating oils, such as naphthene-based lubricating oils, paraffin-based lubricating oils and mixed-base lubricating oils, other hydrocarbon lubricants, for example lubricating oils derived from coal products, and synthetic oils, for example, alkylene polymers, polymers of the alkylene oxide type and their derivatives, including alkylene oxide polymers prepared by polymerizing the alkylene oxide in the presence of water or of alcohols, for example, ethyl alcohol, esters of dicarboxylic acids, liquid esters of phosphorus-containing acids, alkylbenzenes and dialkylbenzenes, polyphenyls, alkyl-diphenyl-ethers and polymers of silicon.

The amount of new compositions or additives to be added depends on the future use of the lubricating oil which is to be upgraded; thus, for an oil for a petrol engine, the amount of additive to be introduced will be from 1 to 7%, for an oil for a diesel engine, it will be from 4 to 10%.

The upgraded lubricating oils can also contain antioxidant adjuvants, anti-corrosion adjuvants and the like.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLE 1

900 g. of polyisobutenylsuccinic anhydride (PIBSA) of acid number 74 (expressed as mg. of potassium hydroxide required to neutralize 1 g. of product), obtained by condensation of maleic anhydride with a polyisobutene of molecular weight about 1,000 are introduced into a 2 liter three-neck flask.

The mixture is heated to 120° C. while stirring, and 58 g. of tris-(6-amino-3-oxa-hexyl)-amine, which corresponds to a molar ratio of polyamine to PIBSA of 0.3, are then added over the course of 1 hour.

The temperature is raised to 160° C. for 3 hours under a reduced pressure of 50 mm. Hg.

The limpid product obtained consists predominantly of tris-polyisobutenylsuccinimide and contains a total nitrogen percentage of 1.06.

EXAMPLE 2

300 g. of PIBSA of acid number equal to 74, obtained from a polyisobutene of molecular weight about 1,000, and 72 g. of oil 100 N as a diluent, are introduced into a 1 liter three-neck flask.

The mixture is heated to 150° C. while stirring, 32 g. of tris-(6-amino-3-oxa-hexyl)-amine, corresponding to a molar ratio of polyamine to PIBSA of 0.5, are added in the course of 1 hour, and the temperature is then maintained for 2 hours under a reduced pressure of 50 mm. Hg.

The limpid product obtained consists predominantly of bis-polyisobutenylsuccinimide and contains a total nitrogen percentage of 1.3%.

The tris-(6-amino-3-oxa-hexyl)-amine employed to obtain the products of these two examples was beforehand prepared as follows by cyanoethylation of triethanolamine with acrylonitrile and hydrogenation of the trinitrile obtained.

894 g. (6mols) of triethanolamine and 9 cm.³ (0.09 mol) of an aqueous sodium hydroxide solution of 36° Be strength are introduced into a 3 liter glass reactor equipped with a mechanical stirrer, a reflux condenser, a dropping funnel and a thermometer, the whole being kept under a nitrogen atmosphere.

954 g. (18 mols) of acrylonitrile are then run gradually, over the course of 1 hour, 20 minutes, into the reaction mixture, which is stirred vigorously and kept at a temperature of 35°–40° C.

When the addition of the acrylonitrile has ended, the reaction mixture is cooled to 20°–25° C., the sodium hydroxide is then neutralized by means of 10 cm.³ of hydrochoric acid (density 1.19) and the sodium chloride is filtered off.

1,851 g. of crude trinitrile, which is in the form of a light yellow limpid liquid, are obtained.

600 cm.³ of a suspension of Raney nickel in absolute ethanol, containing 185 g. of Raney nickel, are introduced, under a nitrogen atmosphere, into a 3.61 stainless steel autoclave equipped with a stirrer system, an injection loop and a thermocouple, and 3 cm.³ of an aqueous sodium hydroxide solution of 36° Be strength are then added. After closing the autoclave, the latter is flushed with nitrogen and then with hydrogen. The stirrer is then started and hydrogen is introduced into the autoclave until a pressure of 25 bars is obtained.

The autoclave is heated to a temperature of 60° C., 1,200 cm.³ of a solution of 616 g. of crude trinitrile in absolute ethanol are then injected over the course of 4 hours, 15 minutes, the injection loop is then rinsed with 100 ml. of absolute ethanol over the course of 20 minutes, and the mixture is allowed to react for a further 30 minutes.

At the end of this time, the autoclave is cooled to about 25° C. and then degassed, flushed with nitrogen and opened.

The reaction mixture is recovered and the reactor is washed with 3 times 200 cm.³ of ethanol. The catalyst is filtered off and 2,070 g. of a light yellow limpid filtrate are obtained. The sodium hydroxide introduced initially is neutralized with 3 cm.³ of hydrochloric acid (d = 1.19) and the filtrate is then concentrated by heating (85°–90° C.) under reduced pressure (15 mm. of mercury).

555 g. of crude amine are obtained and are initially subjected to a first distillation so as to remove the nonvolatile products. The distillation is carried out in a 1 liter boiler equipped with a Vigreux column.

421 g. of oily liquid distilling at a temperature below 215° C. under at most 6 mm. of mercury are collected.

In a second stage, the liquid obtained is rectified in a 1 liter boiler surmounted by a column packed with glass rings.

275.9 g. of tris-(3-oxa-6-amino-hexyl)-amine are collected, distilling from 192 to 201° C. under a pressure of 2 mm. of mercury and having a refractive index $n_D^{25}$ equal to 1.4822.

The purity of the product is determined by nitrogen determination, and amounts to 97.5%.

EXAMPLE 3

1,320 g. of PIBSA of acid number equal to 85, obtained from a polyisobutene of molecular weight approximately equal to 940, are introduced into a 2 liter three-neck flask.

The mixture is heated to 160° C. and 124 g. of N-ethyl-N,N-bis-(6-amino-3-oxa-hexyl)-amine, which corresponds to a molar ratio of polyamine to PIBSA of 0.5, are then added over the course of 1 hour.

The temperature is maintained for 2 hours under a pressure of 50 mm. Hg.

The product obtained consists predominantly of bis-polyisobutenylsuccinimide, contains a nitrogen percentage of 1.54% and has a viscosity of 470 cst at 210° F.

The N-ethyl-N,N-bis-(6-amino-3-oxa-hexyl)-amine employed in this example was prepared beforehand as follows, by cyanoethylation of N-ethyldiethanolamine with acrylonitrile and hydrogenation of the dinitrile obtained.

1,330 g. (10 mols) of N-ethyldiethanolamine and 10 cm.$^3$ (0.1 mol) of an aqueous sodium hydroxide solution of 36° Be strength are introduced into a 3 liter glass reactor under a nitrogen atmosphere.

1.060 g. (20 mols) of acrylonitrile are then run gradually, over the course of 1 hour, into the reaction mixture while stirring and maintaining a temperature of 35°–40° C.

When the acrylonitrile has been added, the reaction mixture is cooled to 20°–25° C., the sodium hydroxide is then neutralized with 10.5 cm.$^3$ of hydrochloric acid (density 1.19) and the sodium chloride is filtered off.

2,386 g. of crude dinitrile which is in the form of a yellow-colored limpid liquid are obtained.

600 cm.$^3$ of a suspension of Raney nickel in absolute ethanol, containing 179 g. of Raney nickel, are introduced into a 3.6 liter stainless steel autoclave under a nitrogen atmosphere, and 3 cm.$^3$ of sodium hydroxide solution of 36° Be strength are added. After closing the autoclave, the latter is flushed with nitrogen and then with hydrogen. The stirring is then started, hydrogen is admitted under a constant pressure of 25 bars, and the mixture is heated to 60° C.

At this temperature, 597.5 g. of crude dinitrile dissolved in 1,200 cm.$^3$ of absolute ethanol are injected over the course of 4 hours, 10 minutes.

The subsequent operations are carried out as described above, 753.5 g. of crude amine are obtained and from this it is possible to obtain, after a first distillation, 516.2 g. of an oily liquid distilling at a temperature below 230° C. under at most 5 mm. of mercury.

After rectifying the liquid obtained, 443.5 g. of N,N-bis-(3-oxa-6-amino-hexyl)-ethylamine are collected, distilling from 125° to 130° C. under a pressure of 1 to 3 mm. of mercury and having a refractive index $n_D^{25}$ of 1.4685.

The purity of the product, determined by nitrogen determination, amounts to 99.7%.

EXAMPLE 4

320 g. of polyisobutenylsuccinic anhydride (PIBSA) of acid number equal to 74 (expressed in mg. of potassium hydroxide required to neutralize 1 g. of product), obtained by condensation of maleic anhydride with a polyisobutene of molecular weight about 1,000, are introduced into a 2 liter three-neck flask.

The mixture is heated to 120° C. while stirring, and 26.3 g. of N,N-bis-(6-amino-3-oxa-hexyl)-N-(2-hydroxyethyl)-amine, which corresponds to a molar ratio of polyamine to PIBSA of 0.5, are then added to the course of 1 hour.

The temperature is raised to 150° C. for 3 hours under a pressure of 20 mm. Hg.

The limpid product obtained consists predominantly of bis-polyisobutenylsuccinimide and contains a total nitrogen percentage of 1.2.

The N,N-bis-(6-amino-3-oxa-hexyl)-N-(2-hydroxyethyl)-amine employed to obtain the products of these two examples was prepared beforehand as follows, by cyanoethylation of triethanolamine to acrylonitrile of 1, followed by hydrogenation of the nitrile obtained.

300 g. of triethanolamine (2 mols) and 3 ml. of commercial sodium hydroxide solution (36° Be strength) are introduced into a 2 liter flask equipped with a central stirrer, a dropping funnel, a condenser and a thermometer. The temperature is raised to 40° C. and 102 g. of acrylonitrile (2 mols) are run in over the course of 12 minutes while maintaining the temperature at 40° C. When all has been run in, 3.5 ml. of 10 N HCl are introduced rapidly. The mixture obtained is then hydrogenated under the following conditions:

154 g. of Raney nickel suspended in 700 cm.$^3$ of ethanol and 12 ml. sodium hydroxide solution (36° Be strength) are introduced into a 3.6 liter autoclave fitted with a central anchor stirrer. After closing the autoclave, the latter is flushed with nitrogen and then with hydrogen, and the hydrogen pressure is raised to 40 bars and the temperature to 60° C.

380 g. of the cyanoethylation mixture obtained above, in solution in 400 cm.$^3$ of alcohol, are now injected; the duration of the injection is 62 minutes. 85 liters of hydrogen were thus absorbed, that is to say, 3.80 mols (S.T.P. conditions), which represents 101% of theory.

The mixture is allowed to cool to ambient temperature, the crude reaction mixture is withdrawn from the autoclave, the catalyst is filtered off, and the alcohol is driven off by distillation under atmospheric pressure and then under 15 mm. up to 130° C. in a boiler.

382 g. of a mixture which is analyzed by gas phase chromatography are thus obtained.

it is found that this mixture consists of 43% of triethanolamine, 0.5% of a product of the formula (OH—CH$_2$—CH$_2$)$_2$N—CH$_2$—CH$_2$—O—CH$_2$—CH$_2$—CH$_2$—NH$_2$, 51% of a product of the formula OH—CH$_2$—CH$_2$—(N—CH$_2$—CH$_2$—O—CH$_2$—CH$_2$—CH$_2$—NH$_2$)$_2$ and 1.5% of tris-(3-oxa-6-amino-hexyl)-amine.

The sodium hydroxide solution is then neutralized, after which the said mixture is distilled under 2mm. of mercury. N,N-Bis-(6-amino-3-oxa-hexyl)-N-(2-hydroxyethyl)-amine is thus obtained in 98% purity.

EXAMPLE 5

Polyisobutenylsuccinimides are prepared in accordance with the procedure described in Example 4 from 114 g. of a mixture based on N,N-bis-(6-amino-3-oxa-hexyl)-N-(2-hydroxyethyl)-amine, referred to as "A" (in an amount of 31–32%) and tris-(6-amino-3-oxa-hexyl)-amine, referred to as "B" (in an amount of 69–68%), and 1,600 g. of PIBSA of acid number equal to 74.

The product obtained is clear and contains a total nitrogen percentage of 1.13; it consists approximately of 31—32% of bis-polyisobutenylsuccinimide derived from "A" and 69–68% of tris-polyisobutenylsuccinimide derived from "B".

The mixture based on amines "A" and "B" employed to obtain the product of this example was prepared beforehand as follows, by cyanoethylation of triethanolamine with acrylonitrile, in a molar ratio of triethanolamine to acrylonitrile of 0.36.

The cyanoethylation operation described in Example 4 is carried out, employing 894 g. (6 mols) of triethanolamine and 878 g. (16.6 mols) of acrylonitrile.

The hydrogenation operation is carried out in accordance with the procedure of Example 1, on 616 g. of the cyanoethylation mixture obtained, in 700 cm.$^3$ of alcohol.

After filtering off the catalyst and evaporating the alcohol, a mixture wherein the proportions of "A" and "B" are respectively 31-32% and 69-68% is obtained.

EXAMPLE 6

Polyisobutenylsuccinimides are prepared in accordance with the procedure described in Example 4, from 118 g. of a mixture containing 50% of amine "A" and 50% of amine "B", and 1,600 g. of PIBSA of acid number equal to 74.

The product obtained is clear and contains a total nitrogen percentage of 1.16; it consists approximately of 50% of bis-polyisobutenylsuccinimide derived from "A" and 50% of tris-polyisobutenylsuccinimide derived from "B".

The tris-(6-amino-3-oxa-hexyl)-amine employed can be prepared in accordance with the procedure described in Example 1.

EXAMPLE 7

Polyisobutenylsuccinimides are prepared in accordance with the procedure described in Example 4 from 109 g. of a mixture containing 10% of amine "A" and 90% of amine "B" and 1,600 g. of PIBSA of acid number equal to 74.

The product obtained is clear and contains a total nitrogen percentage of 1.11; it consists approximately of 10% of bis-polyisobutenylsuccinimide derived from "A" and 90% of tris-polyisobutenylsuccinimide derived from "B".

The tris-(6-amino-3-oxa-hexyl)-amine employed can be prepared in accordance with the procedure described in Example 1.

EXAMPLE 8

523 g. of PIBSA of acid number equal to 74 are introduced into a 1 liter three-neck flask. The mixture is heated to 140° C. while stirring, and 69 g. of N-ethyl-N-(2-hydroxyethyl)-N-(6-amino-3-oxa-hexyl)-amine are then added, which corresponds to a molar ratio of polyamine to PIBSA of 1.

The temperture is raised to 150° C. for 3 hours under 20 mm. Hg.

The product obtained is limpid and consists predominantly of monopolyisobutenylsuccinimide and contains a total nitrogen percentage of 1.77.

The N-ethyl-N-(2-hydroxyethyl)-N-(6-amino-3-oxa-hexyl)amine employed to obtain the product of this example was prepared beforehand as follows, by cyanoethylation of ethyldiethanolamine with acrylonitrile in a molar ratio of ethyldiethanolamine to acrylonitrile of 1 to 0.66, followed by hydrogenation of the nitrile obtained.

The cyanoethylation procedure described in Example 4 is carried out, employing 532 g. of ethyldiethanolamine (4 mols) and 141 g. of acrylonitrile (2.66 mols).

The hydrogenation operation is carried out in accordance with the procedure of Example 4, on 616 g. of the cyanoethylation mixture obtained, in 700 cm.³ of alcohol. The amount of hydrogen absorbed is 115 liters, that is to say, 5.13 mols (S.T.P. conditions), representing 96% of the theoretical amount.

After filtering off the catalyst and evaporating the alcohol, 620 g. of crude product are obtained, having the following composition: 33% of ethyldiethanolamine, 55% of the product of the formula

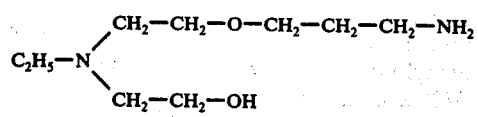

and 9% of the product of the formula

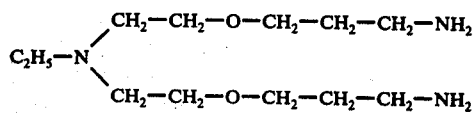

The sodium hydroxide solution is next neutralized and the said mixture is then distilled under 1 mm. Hg. N-ethyl-N-(2-hydroxyethyl)-N-(6-amino-3-oxa-hexyl)-amine is thus obtained in 98% purity.

EXAMPLE 9

Succinimides are prepared in accordance with the procedure described in Example 8 from 138 g. of a mixture of amines comprising 30% of N-ethyl-N-(2-hydroxyethyl)-N-(6-amino-3-oxahexyl)-amine and 70% of N-ethyl-N,N-bis-(6-amino-3-oxa-hexyl)-amine, and 1,600 g. of PIBSA of acid number equal to 74.

The product obtained obtained is clear, contains a total nitrogen percentage of 1.31 and consists of about 30% of bis-polyisobutenyl-succinimide derived from N-ethyl-N-(2-hydroxyethyl)-N-(6-amino-3-oxa-hexyl)-amine and 70% of bis-polyisobutenylsuccinimide derived from N-ethyl-N,N-bis-(6-amino-3-oxa-hexyl)-amine.

The N-ethyl-N,N-bis-(6-amino-3-oxa-hexyl)-amine employed can be prepared in accordance with the procedure described in Example 3.

EXAMPLE 10

The products of the invention obtained in accordance with the examples above were tested with regard to their dispersing properties in the lubricants. The dispersing power was studied in accordance with the spot method described in Volume 1 of the work by A. Schilling, "Les huiles pour moteurs et le graissage des moteurs" (Engine oils and greasing of engines"), 1962 edition, pages 89–90.

The method is carried out starting with 20 g. of SAE 30 oil to which are added 5 g. of a sludge originating from a Petter $AV_1$ engine and containing about 2% of carbonaceous matter.

Additives had beforehand been introduced into the SAE 30 oil in accordance with the following formulation (the amounts of the various additives being given per 1 kg. of oil): 50 mmols of the dispersing agent to be studied, 30 mmols of calcium alkylbenzenesulphonate, 30 mmols of super-alkalinized calcium alkylphenate and 15 mmols of zinc dihexyldithiophosphate.

The weight of the reaction mixture corresponding to 50 mmols of dispersing agent can be calculated as follows:

take 100 g. of a mixture of amines "A" + "B", x is the number of $NH_2$ groups derived from the amine "A" in 100 g. of the mixture of amines, y is the number of $NH_2$ groups derived from the amine "B" in 100 g. of the mixture of amines, and P is the weight of PIBSA employed.

The number of mols of PIBSA which have reacted with 100 g. of the mixture of amines is $x + y$ for example, if all the $NH_2$ groups react with the PIBSA.

In that case, the number of moles of succinimides present in P + 100 g. of reaction mixture is $x + y$.

Accordingly, 50 mmols of dispersing agent correspond to $$\frac{P + 100}{x + y} \times 50.10^{-3} g.$$

of reaction mixture.

The mixture of additive-containing oil and of sludge is separated into 5 fractions which are stirred and subjected to the following 5 heat treatments:
one fraction is heated at 50° C. for 10 minutes,
one fraction is heated at 200° C. for 10 minutes,
one fraction is heated at 250° C. for 10 minutes,
one fraction is heated at 50° C. for 10 minutes in the presence of 1% of water, and
one fraction is heated at 200° C. for 10 minutes in the presence of water.

A drop of each mixture obtained after heat treatment is deposited on a filter paper.

The ratings are determined after 48 hours. For each spot, the percentage of product dispersed relative to the oil spot is calculated by determining the ratio of the rspective diameters of the oil spot and of the dispersed product. The higher is the percentage of dispersed product, the better is the dispersion of the sludge.

The results shown in the Table, below, are thus obtained.

EXAMPLE 11

The anti-rust properties of the products of Examples 1 to 9 are tested in SAE 30 oil into which additives have been introduced in accordance with the formulation of the preceding example, namely, per 1 kg. of oil: 50 mmols of the products of Examples 1 to 9, 30 mmols of calcium alkylbenzenesulphonate, 30 mmols of superalkalinized calcium alkylphenate and 15 mmols of zinc dihexyldithiophoshate.

The principle of this test consists of adding, to the oil to be studied, the products likely to be present in the blow-by gases and playing a role in the formation of rust on the combination of valve lifter and valve stem, and of immersing a piece forming part of the preceding combination for a certain time in the mixture. The rust formed is rated visually.

The test is carried out by introducing 700 g. of oil into a flask, heating it to 50° C. while stirring, successively adding, when the temperature has become stable, 20 cm.³ of a 30% strength aqueous solution of formaldehyde, 4.5 cm.³ of methanol, 5 cm.³ of a 50/50 mixture of dichloroethane and dibromoethane and 8.5 cm.³ of a 78.5% strength aqueous solution of nitric acid, and immersing a piece of the combination of valve lifter and valve stem in the mixture for 19 hours.

If it has not been attacked, the product is given a rating of 20; if the attack is very extensive, it is given a rating of 0.

The results of the assessments are shown in the Table, below.

EXAMPLE 12

The anti-foam properties of the products of Examples 1 to 9 are measured in accordance with standard specification ASTM D 892.63 in SAE 30 oil into which additives have been introduced in accordance with the formulation indicated in Examples 10 and 11.

The results of the assessments are shown in the Table, below.

TABLE

| PRODUCTS | | PERFORMANCES | | |
|---|---|---|---|---|
| | | Dispersion | Anti-rust | Anti-foam |
| From Example | 1 | 470 | 16 | 10-05 |
| " | 2 | 430 | 14 | 10-05 |
| " | 3 | 410 | 14 | 10-05 |
| " | 4 | 430 | 18 | 10-05 |
| " | 5 | 450 | 17 | 10-05 |
| " | 6 | 440 | 17 | 10-05 |
| " | 7 | 470 | 17 | 10-05 |
| " | 8 | 370 | 17 | 10-05 |
| " | 9 | 390 | 17 | 10-05 |
| I. Comparison | | 400 | 12 | 580-450 |
| II. Comparison | | 380 | 7 | 600-450 |

The products prepared in Examples 5, 6, 7 and 9 can also be prepared by simple mixing of the two succinimides; the results of the dispersion tests, rust tests and foam tests are equivalent to those shown in the final table.

By way of comparison, the above Table shows the results of the tests of the dispersing properties, anti-rust properties and anti-foam properties carried out under the conditions described in Examples 10 to 12 on the preceding succinimides, namely: I. The bis-(polyisobutenylsuccinimide) derived from triethylenetetramine and a PIBSA of acid number 74, obtained by condensation of maleic anhydride and a polyisobutene of molecular weight about 1,000. II. The mono-(polyisobutenylsuccinimide) derived from tetraethylenepentamine and a PIBSA of acid number 74, obtained by condensation of maleic anhydride and a polyisobutene of molecular weight about 1,000.

Polyamines having ether groups of formula II, above, and the novel method of their preparation constitute the subject matter of copending U.S. patent application of Paul Collet, entitled "Compositions Based on Polyamines with Ether Groups", assigned to related company, Rhone-Poulenc Industries.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. New compositions based on alkenylsuccinimides, characterized in that they comprise at least one alkenylsuccinimide of the formula

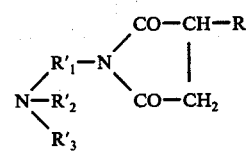

in which formula R is an alkenyl group containing from 20 to 200 carbon atoms, $R'_1$ is a —r—O—r' radical, $R'_2$ is one of the radicals

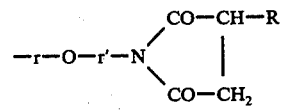

-continued

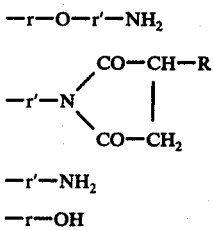

or and R'$_3$ is one of the radicals

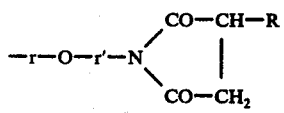

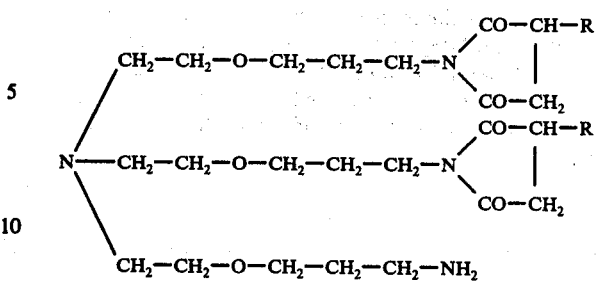

in which formula R is a polyisobutenyl radical containing from 20 to 200 carbon atoms.

5. A composition according to claim 1, comprising an alkenylsuccinimide of the formula:

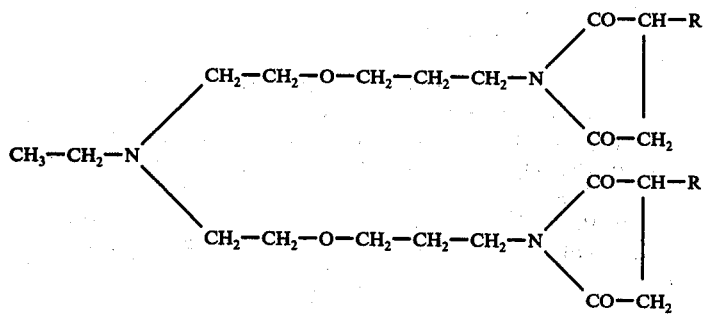

in which the formula R is a polyisobutenyl radical containing from 20 to 200 carbon atoms.

6. A composition according to claim 1, comprising an alkenylsuccinimide of the formula:

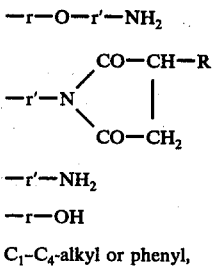

$C_1$-$C_4$-alkyl or phenyl, the radical r representing an optionally branched $C_2$-$C_3$-alkyl group and the radical r' representing a propyl or isobutyl group.

2. A composition according to claim 1, wherein the radical r represents an ethyl or isopropyl group.

3. A composition according to claim 1, comprising an alkenylsuccinimide of the formula:

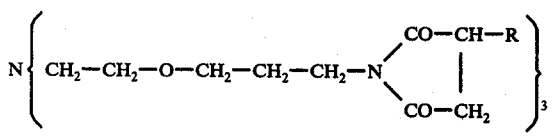

in which formula R is a polyisobutenyl radical containing from 20 to 200 carbon atoms.

4. A composition according to claim 1, comprising an alkenylsuccinimide of the formula:

in which formula R is a polyisobutenyl radical containing from 20 to 200 carbon atoms.

7. A composition according to claim 1, comprising an alkenylsuccinimide of the formula:

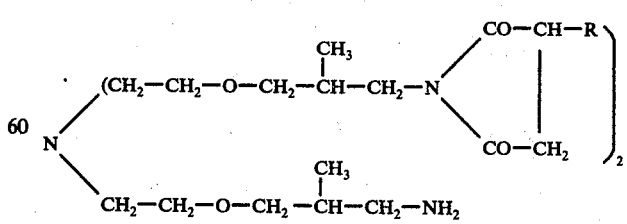

in which formula R is a polyisobutenyl radical containing from 20 to 200 carbon atoms.

8. A composition according to claim 1, comprising an alkenylsuccinimide of the formula:

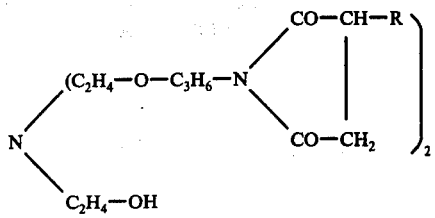

in which formula R represents a polyisobutenyl radical containing from 20 to 200 carbon atoms.

9. A composition according to claim 1, comprising an alkenylsuccinimide of the formula:

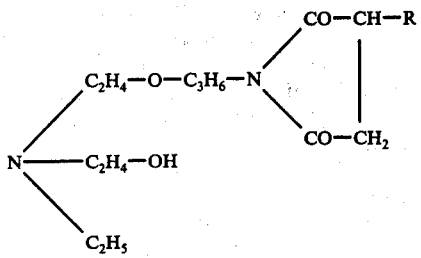

in which formula R represents a polyisobutenyl radical containing from 20 to 200 carbon atoms.

10. A process for the preparation of a composition according to claim 1, characterized in that an alkenylsuccinic anhydride in which the alkenyl group contains from 20 to 200 carbon atoms is condensed, at a temperature of between 120 and 230° C., with at least one polyamine of the formula:

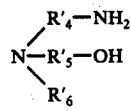

in which formula R′₄ is a —r—O—r′ radical, R′₅ is one of the radicals —r—O—r′—NH₂, —r′—NH₂, or —r—OH, R′₆ is one of the radicals —r—O—r′—NH₂, —r′—NH₂, —r—OH, C₁-C₄-alkyl or phenyl, using a molar ratio of polyamine to alkenylsuccinic anhydride of less than 1.

11. A process according to claim 10, wherein the radical r represents an ethyl or isopropyl group.

12. A process according to claim 10, wherein a polyisobutenylsuccinic anhydride in which the alkenyl group contains from 20 to 200 carbon atoms is condensed, at a temperature of between 140° and 180° C., with tris-(6-amino-3-oxahexyl)-amine, using a molar ratio of polyamine to polyisobutenylsuccinic anhydride of between 0.3 and 0.35.

13. A process according to claim 10, wherein a polyisobutenylsuccinic anhydride in which the alkenyl group contains from 20 to 200 carbon atoms is condensed, at a temperature of between 140° and 180° C., with tris-(6-amino-3-oxahexyl)-amine, using a molar ratio of polyamine to polyisobutenylsuccinic anhydride of between 0.4 and 0.6.

14. A process according to claim 10, wherein a polyisobutenylsuccinic anhydride in which the alkenyl group contains from 20 to 200 carbon atoms is condensed, at a temperature of between 140° and 180° C., with N-ethyl-N,N-bis-(6-amino-3-oxa-hexyl)-amine, using a molar ratio of between 0.4 and 0.6.

15. A process according to claim 10, wherein a polyisobutenylsuccinic anhydride in which the alkenyl group contains from 20 to 200 carbon atoms is condensed, at a temperature of between 140° and 180° C., with tris-(3-oxa-5-methyl-6-amino-hexyl)-amine, using a molar ratio of polyamine to polyisobutenylsuccinic anhydride of between 0.3 and 0.35.

16. A process according to claim 10, wherein a polyisobutenylsuccinic anhydride in which the alkenyl group contains from 20 to 200 carbon atoms is condensed, at a temperature of between 140° and 180° C., with tris-(3-oxa-5-methyl-6-amino-hexyl)-amine, using a molar ratio of polyamine to polyisobutenylsuccinic anhydride of between 0.4 and 0.6.

17. A process according to claim 10, wherein a polyisobutenylsuccinic anhydride in which the isobutenyl group contains from 20 to 200 carbon atoms is condensed at a temperature of between 140° and 180° C., with N-(2-hydroxyethyl)-N,N-bis-(3-oxa-7-amino-hexyl)-amine, using a molar ratio of polyamine to polyisobutenylsuccinic anhydride of between 0.4 and 0.6.

18. A process according to claim 10, wherein a polyisobutenylsuccinic anhydride in which the isobutenyl group contains from 20 to 200 carbon atoms is condensed, at a temperature of between 140° and 180° C., with N-ethyl-N-(2-hydroxyethyl)-N-(6-amino-3-oxa-hexyl)-amine, using a molar ratio of polyamine to polyisobutenylsuccinic anhydride of between 0.8 and 0.95.

19. A composition based on alkenylsuccinimide according to claim 1, characterized in that it comprises at least one of the alkenylsuccinimides of the formula

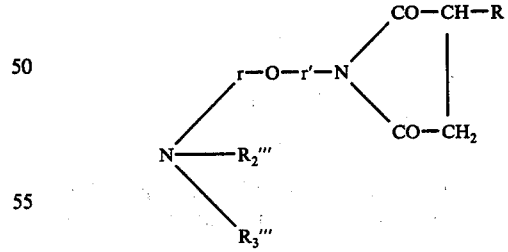

in which formula R″₂ represents the radical

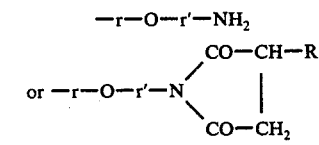

and R″₃ represents one of the radicals

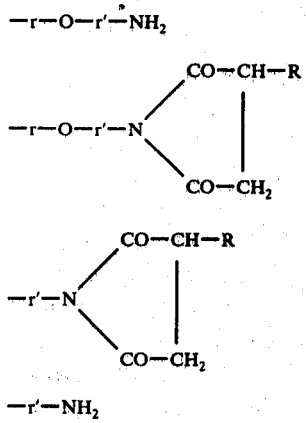

$C_1$–$C_4$—alkyl or phenyl, and at least one of the alkenylsuccinimides of the formula

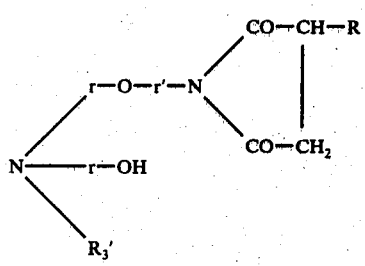

in which formula R represents an alkenyl group containing from 20 to 200 carbon atoms and $R'_3$ represents one of the radicals

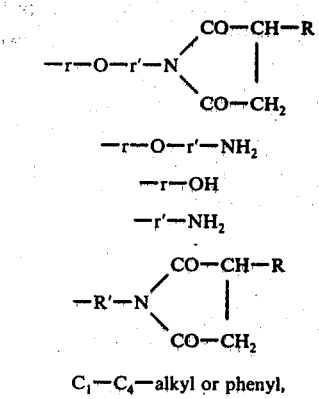

$C_1$–$C_4$—alkyl or phenyl, the radical r representing an optionally branched $C_2$-$C_3$- alkyl group and the radical r' representing a propyl or isobutyl group.

20. A composition according to claim 19, characterized in that they contain from 98 to 50% of at least one polyisobutenylsuccinimide of the formula

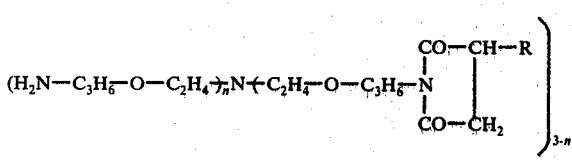

where n is equal to 0, 1 or 2 and R represents a polyisobutenyl radical containing from 20 to 200 carbon atoms, and from 2 to 50% of at least one polyisobutenylsuccinimide of the formula

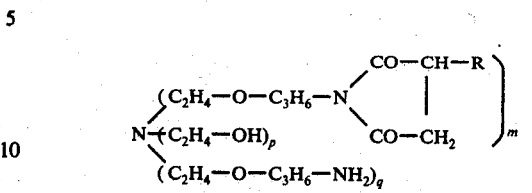

where m and p are equal to 1 or 2 and q is equal to 3-(m+p).

21. A process according to claim 10, wherein a polyisobutenylsuccinic anhydride in which the alkenyl group contains from 20 to 200 carbon atoms is condensed, at a temperature of between 140 and 180° C., with a composition based on polyamines with ether groups, consisting of 98 to 50%, of its weight, of tris-(3-oxa-6-amino-hexyl)-amine and of 2 to 50%, of its weight of N-(2-hydroxyethyl)-N,N-bis-(6-amino-3-oxa-hexyl)-amine and of N,N-bis-(2-hydroxyethyl)-N-(6-amino-3-oxa-hexyl)-amine.

22. A composition according to claim 19, characterized in that they contain from 98 to 50% of at least one polyisobutenylsuccinimide of the formula

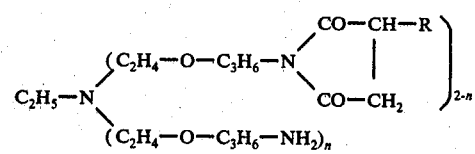

in which formula n is equal to 0 or 1, and from 2 to 50% of a polyisobutenylsuccinimide of the formula

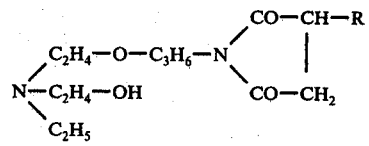

where R represents a polyisobutenyl radical containing from 20 to 200 carbon atoms.

23. A process according to claim 10, wherein a polyisobutenylsuccinic anhydride in which the alkenyl group contains from 20 to 200 carbon atoms is condensed, at a temperature of between 140° and 180° C., with a composition based on polyamines with ether groups, consisting of 98 to 50%, of its weight, of N,N-bis-(3-oxa-6-amino-hexyl)-ethylamine and 2 to 50% of N-ethyl-N-(2-hydroxyethyl)-N-(6-amino-3-oxa-hexyl)-amine.

24. A lubricating oil composition comprising a major proportion of an oil of lubricating viscosity containing from about 1 to 10% by weight of a composition according to claim 1.

25. A lubricating oil composition comprising a major proportion of an oil of lubricating viscosity containing from about 1 to 10% by weight of a composition according to claim 6.

26. A lubricating oil composition comprising a major proportion of an oil of lubricating viscosity containing from about 1 to 10% by weight of a composition according to claim 7.

* * * * *

UNITED STATES PATENT AND TRADEMARK OFFICE
CERTIFICATE OF CORRECTION

PATENT NO. : 4,081,388
DATED : March 28, 1978
INVENTOR(S) : Gerard Soula et al.

It is certified that error appears in the above-identified patent and that said Letters Patent are hereby corrected as shown below:

Col. 3, line 16, delete "chorine" and replace with
-- chlorine --.

Col. 3, line 27, delete "tris-(3-oxo-" and replace with
-- tris-(3-oxa- --.

Col. 5, line 65, delete "R'$_3$'" and replace with
-- R"$_3$' --.

Col. 11, line 43, delete "temperture" and replace with
-- temperature --.

Col. 12, line 27, delete "obtained", second occurrence.

Col. 13, line 28, delete "rspective" and replace with
-- respective --.

Col. 18, line 27, delete "7-amino" and replace with
-- 6-amino --.

UNITED STATES PATENT AND TRADEMARK OFFICE
CERTIFICATE OF CORRECTION

PATENT NO. : 4,081,388
DATED : March 28, 1978
INVENTOR(S) : Gerard Soula et al.

It is certified that error appears in the above-identified patent and that said Letters Patent are hereby corrected as shown below:

Col. 18, line 42, after "on" insert -- an --.

Col. 18, formula between lines 50-55, delete "$R_2'''$ " and replace with -- $R''_2$ --.

Col. 19, line 50, delete "-R'-" and replace with -- -r'- --.

Signed and Sealed this

Eighth Day of August 1978

[SEAL]

Attest:

RUTH C. MASON
Attesting Officer

DONALD W. BANNER
Commissioner of Patents and Trademarks